United States Patent [19]

Bowman et al.

[11] Patent Number: 5,399,171
[45] Date of Patent: Mar. 21, 1995

[54] INTRAVENOUS METERING MONITORING DEVICE

[75] Inventors: George A. Bowman, Vernon Hills; Leonard F. Goloski, Sr., McHenry, both of Ill.

[73] Assignee: Baxter International Inc., Deerfield, Ill.

[21] Appl. No.: 39,710

[22] Filed: Apr. 1, 1993

Related U.S. Application Data

[63] Continuation of Ser. No. 712,850, Jun. 10, 1991, abandoned.

[51] Int. Cl.⁶ ............................................. A61M 31/00
[52] U.S. Cl. ................................................... 604/247
[58] Field of Search ............ 604/122, 153, 154, 65-67, 604/245-247; 128/DIG. 12, DIG. 13

[56] References Cited

U.S. PATENT DOCUMENTS

| | | |
|---|---|---|
| 3,620,650 | 11/1971 | Shaw . |
| 4,126,132 | 11/1978 | Portner et al. . |
| 4,140,118 | 2/1979 | Jassawalla . |
| 4,142,524 | 3/1979 | Jassawalla et al. . |
| 4,217,993 | 8/1980 | Jess et al. ............... 128/DIG. 13 |
| 4,276,004 | 6/1981 | Hahn . |
| 4,277,227 | 7/1981 | Jenkins . |
| 4,336,800 | 6/1982 | Giovanni . |
| 4,444,546 | 4/1984 | Pazemenas . |
| 4,453,931 | 6/1984 | Pastrone . |
| 4,453,932 | 6/1984 | Pastrone . |
| 4,457,753 | 7/1984 | Pastrone ........................ 604/153 |
| 4,470,758 | 9/1984 | Pazemenas et al. . |
| 4,474,309 | 10/1984 | Solomon . |
| 4,487,601 | 12/1984 | Lindemann .............. 128/DIG. 13 |
| 4,557,725 | 12/1985 | Heyne et al. . |
| 4,565,500 | 1/1986 | Jeensalute et al. .................. 604/67 |
| 4,648,869 | 3/1987 | Bobo, Jr. . |
| 4,684,364 | 8/1987 | Sawyer et al. . |
| 4,718,576 | 1/1988 | Tamura et al. . |
| 4,758,228 | 7/1988 | Williams ..................... 128/DIG. 12 |
| 4,784,643 | 11/1988 | Siretchi et al. ..................... 604/65 |
| 4,846,792 | 7/1989 | Bobo, Jr. et al. . |
| 4,856,339 | 8/1989 | Williams ..................... 128/DIG. 13 |
| 4,919,596 | 4/1990 | Slate et al. ........................ 604/154 |
| 4,959,050 | 9/1990 | Bobo, Jr. . |
| 4,979,940 | 12/1990 | Bobo, Jr. et al. . |
| 4,981,467 | 1/1991 | Bobo, Jr. et al. . |
| 5,026,348 | 6/1991 | Venegas ........................... 604/122 |
| 5,039,279 | 8/1991 | Natwick et al. . |
| 5,055,001 | 10/1991 | Natwick et al. . |

FOREIGN PATENT DOCUMENTS

| | | |
|---|---|---|
| 0121931 | 10/1984 | European Pat. Off. . |
| 0291727 | 11/1988 | European Pat. Off. . |
| 0429866 | 6/1991 | European Pat. Off. . |
| 9007942 | 7/1990 | WIPO . |

*Primary Examiner*—John D. Yasko
*Assistant Examiner*—Manuel Mendez
*Attorney, Agent, or Firm*—Paul E. Schaafsma; Paul C. Flattery

[57] ABSTRACT

The present invention provides an improved, low cost method and apparatus for monitoring the intravenous metering of fluids to a patient. The present invention provides a strain gauge which is preferably a balanced metal beam. Conditioning circuitry is provided which has as input the strain gauge output. The output of the conditioning circuit is inputted into occlusion sensing circuit. The output of occlusion sensing circuit is inputted into an air sensing circuit. The output of both the occlusion sensing circuit and the air sensing circuit are inputted into an analog to digital convertor which is monitored by a microprocessor for abnormal signals.

10 Claims, 8 Drawing Sheets

INTRAVENOUS METERING MONITORING DEVICE

This is a continuation of application Ser. No. 07/712,850, filed on Jun. 10, 1991, and now abandoned.

FIELD OF THE INVENTION

The present invention relates in general to intravenous metering devices and in particular to an intravenous metering device having improved monitoring. This application is a continuation of Application No. 07/712,850, now abandoned.

BACKGROUND OF THE INVENTION

Considerable attention in recent years has been directed to the intravenous delivery of fluids such as saline solutions and the like to patients. Initially, these fluids were administered to the patient by means of gravity flow from a container holding the fluid to be delivered. Gravity-flow devices, however, can be cumbersome to use, inasmuch as pressure sufficient to sustain fluid movement in a gravity-flow device often required positioning of tile device at a considerable elevation above the patient receiving the fluid. Moreover, attempts to accurately regulate the amount of fluid administered by gravity-flow devices were often unsuccessful because of the fact that the gravity-induced pressure responsible for moving fluid through the device generally decreased during the intravenous delivery operation as the fluid level within the container holding the fluid dropped.

In order to provide for improved flow of fluids to patients, pumping devices have been utilized such as found in U.S. Pat. Nos. 4,336,800; 4,453,931; 4,453,932; 4,457,753; and U.S. Application Ser. No. 07/411,789. Such pumping devices employ a metering device control unit into which an intravenous metering device is placed. The intravenous metering device includes a pumping chamber which includes a reciprocal diaphragm. The metering device includes a pumping piston which reciprocates the diaphragm thereby changing the volume of the pumping chamber. Check valves are positioned at the pumping chamber inlet and outlet to regulate the flow of fluid and a gas retention chamber is provided upstream of the pumping chamber and the pumping chamber inlet. The gas retention chamber is connected via tubing to a fluid source while the pumping chamber outlet is connected to a patient.

SUMMARY OF THE INVENTION

The present invention provides an improved, low cost method and apparatus for monitoring the intravenous metering of fluids to a patient. The present invention provides a strain gauge which is preferably a balanced metal beam. Conditioning circuitry is provided which has as input the strain gauge output. The output of the conditioning circuit is inputted into occlusion sensing circuit. The output of the occlusion sensing circuit is inputted into an air sensing circuit. The output of both the occlusion sensing circuit and the air sensing circuit are inputted into an analog to digital convertor which is monitored by a microprocessor for abnormal signals.

DETAILED DESCRIPTION OF A PREFERRED EMBODIMENT

Figure 1:
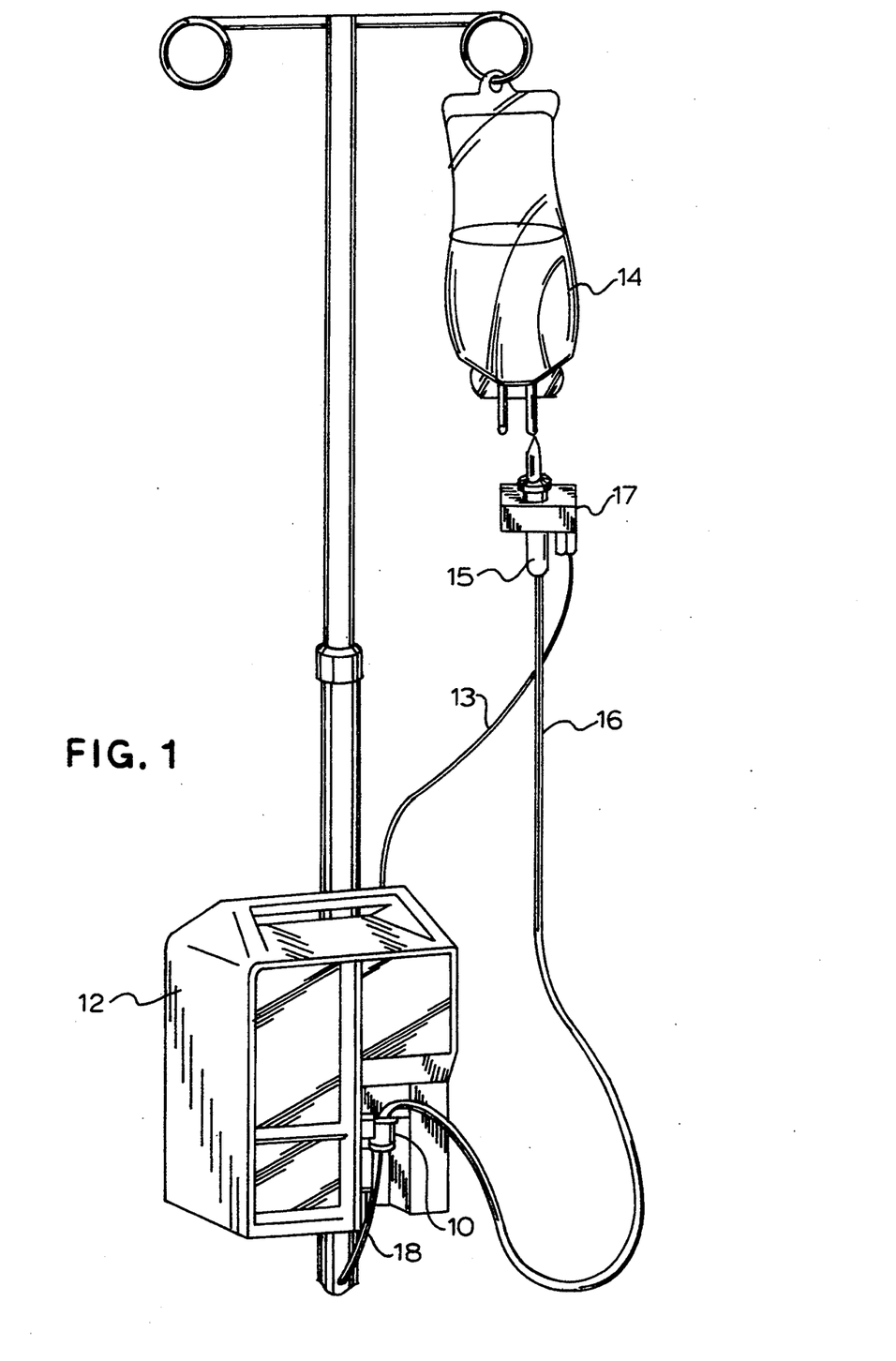
FIG. 1 is a perspective view of a pumping apparatus which uses an intravenous metering device.

Referring first to FIG. 1, an intravenous metering device 10 is shown positioned within a metering device control unit 12. The intravenous metering device 10 in conjunction with the metering device control unit 12 acts as a pump means to transfer fluid from a source of fluid 14 to a patient. The intravenous metering device 10 is connected to the source of fluid 14 by means of conventional tubing 16. Additional tubing 18, extending from the outlet of intravenous metering device 10, transfers precise amounts of fluid to the patient.

Provided between the container of fluid 14 and the tubing 16 is a conventional drip chamber 15. The drip chamber 15 is partially surrounded by a drop sensing means 17 which senses the drops passing in the drip chamber 15. The drop sensing means 17 can be connected to the metering device control unit 12 by wiring 13 so that, if the absence of drops is sensed, an alarm in the metering device control unit 12 can be sounded.

Figure 2:
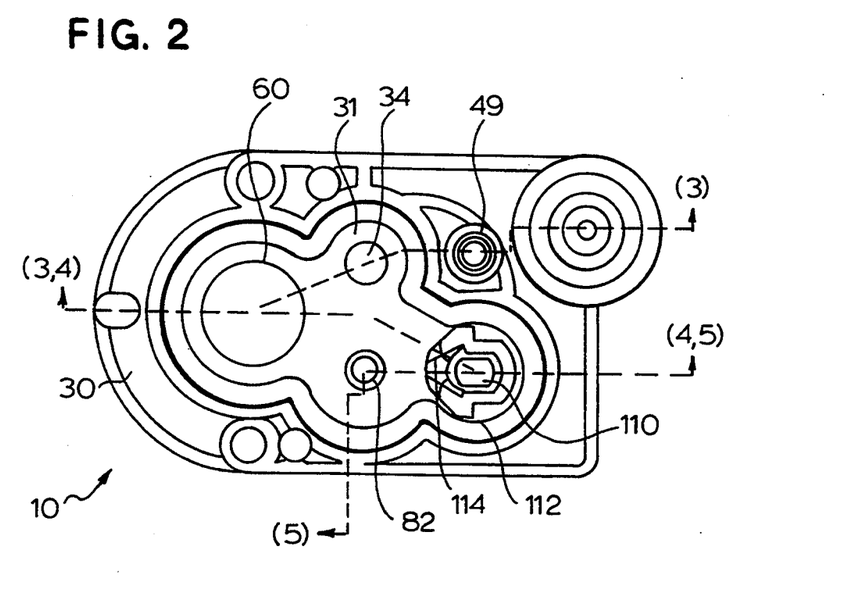
FIG. 2 is a top view of an intravenous metering device.
Figure 3:
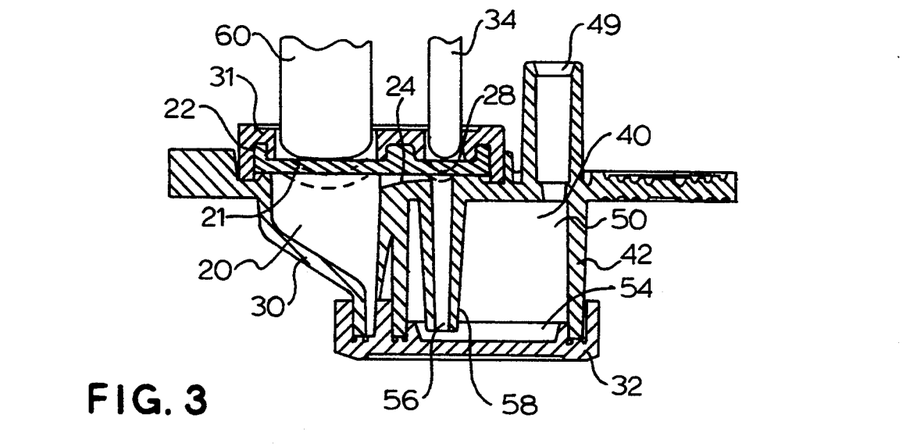
FIG. 3 is a cross-sectional view of the device of FIG. 2 taken along line III—III of FIG. 2.
Figure 4:
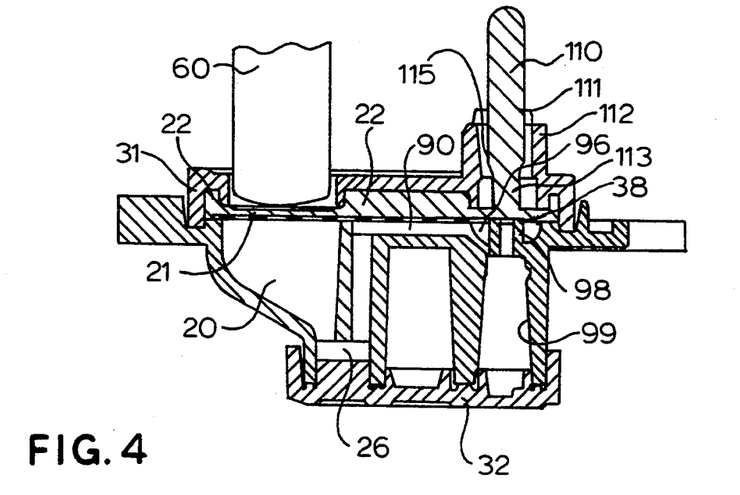
FIG. 4 is a cross-sectional view of the device of FIG. 2 taken along line IV—IV of FIG. 2.

Referring now to FIGS. 2 thru 6, construction of an intravenous metering device 10 is shown in detail. The intravenous metering device 10 includes a pumping chamber 20 formed in housing 30 and a flexible diaphragm 22 which forms an upper portion 21 of pumping chamber 20. The housing 30 includes a housing lid 31 as well as a housing bottom 32. A pumping chamber inlet 24 and a pumping chamber outlet 26 are formed in pumping chamber 20. Pumping chamber 24 includes a valve seat means 28. Valve actuator 34 controls the admission of fluid into pumping chamber 20 by reciprocating the diaphragm 22 between an open position, shown in solid lines in FIG. 3, and a closed position as shown by dotted lines in FIG. 3. As best seen in FIG. 4, the pumping chamber outlet 26 includes a valve 38 which is normally held in a closed position.

Intravenous metering device 10 further includes a metering device inlet 49 which is disposed above an air retention chamber 40 bounded by housing sidewalls 42. The air retention chamber 40 is of sufficient size to include an air retention chamber upper portion 50 providing for an air-fluid interface. Air retention chamber 40 also includes an air retention chamber lower portion 54 which collects fluid free of air bubbles. The fluid free of air bubbles can then pass through an air retention chamber passageway 56 in tubular conduit 58 past the open valve seat means 28 and on into the pumping chamber 20.

The metering device control unit 12 provides means for varying the volume of the pumping chamber 20 in order to pressurize the pumping chamber 20 to provide fluid propulsion. These means can include means for flexing diaphragm 22 into pumping chamber 20 which in the present invention is a reciprocating pumping piston 60 which presses against flexible diaphragm 22, whereupon fluid free of air bubbles is pumped through the intravenous metering device 10 as described below. The position or diaphragm 22 shown by solid lines in FIG. 3 illustrates the condition of the diaphragm 22 when pumping piston 60 is in the upstroke position while the dotted line position of diaphragm 22 illustrates the position of the diaphragm 22 in the associated down-stroke position of pumping piston 60.

Figure 5:
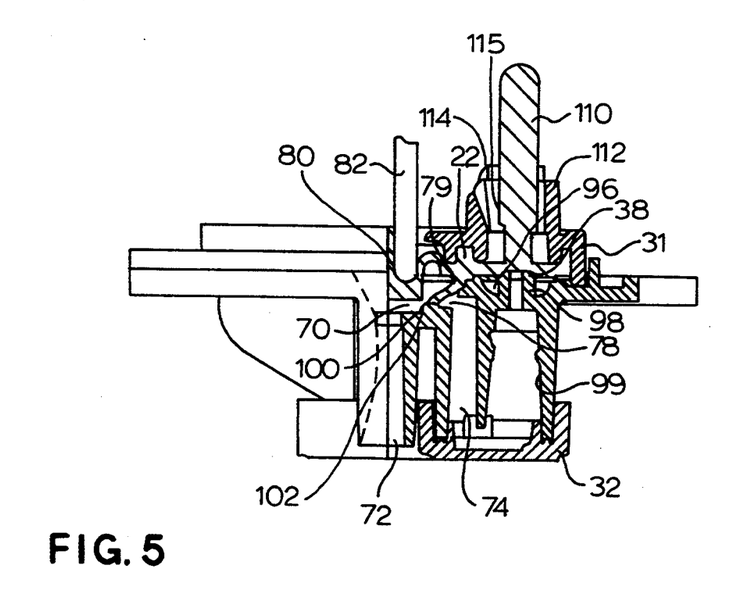
FIG. 5 is a cross-sectional view of the device of FIG. 2 taken along line V—V of FIG. 2.

The intravenous metering device 10 includes a pressure measuring chamber 70 seen in FIG. 5. The pressure measuring chamber 70 is incorporated into the fluid flow path leaving the pumping chamber 20 so that priming will be accomplished in generally the same manner as with the pumping chamber 20. Intravenous metering device 10 is constructed with the pressure measuring chamber 70 and an intravenous metering device outlet 72 positioned at the base of pressure measuring chamber 70. An intermediate passageway 74 is formed to carry fluid from the pumping chamber outlet 26 past valve 38 into the pressure measuring chamber 70 entering at a pressure inlet 78. The intravenous device outlet 72 is located at the bottom of pressure measuring chamber 70 so that the pressure measuring chamber 70 is made a part of the fluid flow path through intravenous metering device 10. The flow of the fluid during the intravenous metering device 10 priming operation described below will continue on into the pressure measuring chamber 70, removing air otherwise present in the intravenous metering device 10 from the pressure measuring chamber 70 as well as the pumping chamber 20.

Pressure pin 82 is oriented over a portion 80 of diaphragm 22 which covers the pressure measuring chamber 70 as shown, and movement of pressure pin 82 in response to upward motion of diaphragm portion 80 can be translated into a pressure reading as will be described in detail below. An elongated passageway 90 is formed in the intravenous metering device 10 to transport fluid from the pumping chamber 20 to the valve 38.

Figure 6A:
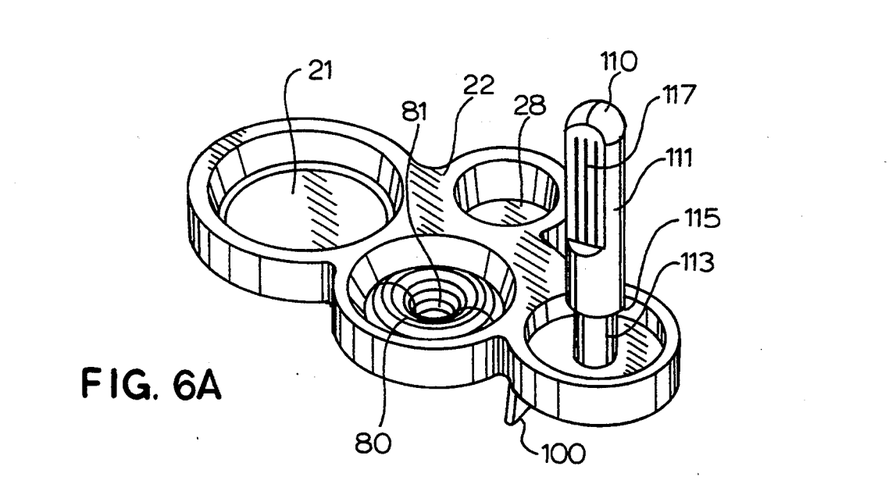
FIG. 6A is an upper perspective view of the diaphragm of an intravenous metering device.
Figure 6B:
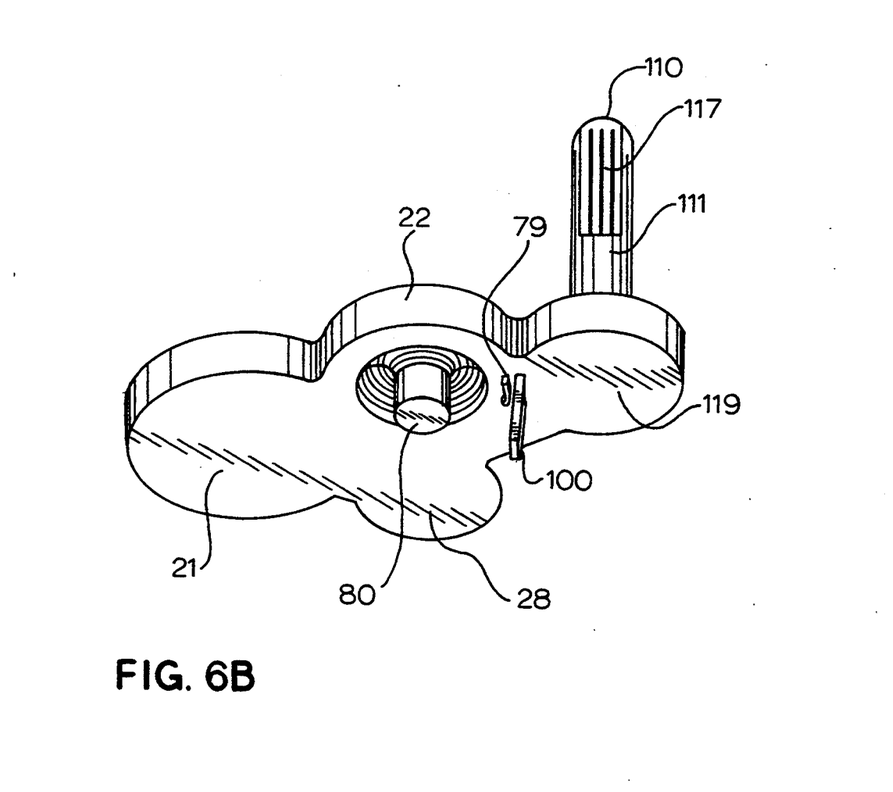
FIG. 6B is a lower perspective view of the diaphragm of an intravenous metering device.

Referring to FIGS. 6A and 6B, a perspective view of the diaphragm 22 is seen in detail, both from above and below. The diaphragm 22 includes the upper portion 21 of pumping chamber 20 which is reciprocal by pumping piston 60 to vary the volume of the pumping chamber 20. The diaphragm 22 also includes the upper portion 80 of the pressure measuring chamber 70. This portion 80 of the diaphragm 22 includes a generally funnel shaped aperture 81 in which pressure pin 82 is held.

Diaphragm 22 further includes valve seat means 28 which, in conjunction with housing 30, forms pumping chamber inlet 24. Valve seat means 28 is reciprocal by valve activator 34 to control admission of fluid into pumping chamber 20.

Extending upwardly from the diaphragm 22 is the integrally formed priming stem 110. The priming stem 100 includes an increased diameter portion 111 and a stem base 113. The junction of the increased diameter portion 111 and stem base 113 defines a stem flange 115. The priming stem 110 further includes a grip portion 117 to aid in user gripping. On the diaphragm opposite the primary stem is standpipe contacting portion 119 which establishes contact with standpipe 98.

Extending downwardly from the diaphragm 22 is an integrally formed flapper valve 100 which forms with a molded ramp 102 on housing 30 a one-way valve. This one-way valve separates the intermediate passageway 74 from the pressure measuring chamber 70. Also extending downwardly is a biasing ridge 79 which acts to bias flapper valve 100 against molded ramp, as seen in FIG. 5.

Referring back to FIGS. 2–5, operation of the intravenous metering device will be described. When pressure is applied to the pumping chamber 20 by the pumping piston 60, the fluid flows from the pumping chamber 20 through the pumping chamber outlet to the elongated passageway 90. An annular outlet pressure chamber 96 is formed at the downstream end of elongated passageway 90 having as its upper wall the diaphragm 22. A standpipe 98 having an aperture 99 defined along its central axis is centered in outlet pressure chamber 96. At its upper periphery, the standpipe 98 is preloaded against the diaphragm 22 thus forming a fluid seal to prevent fluid flow.

When sufficient pressure is generated in pumping chamber 20 and outlet pressure chamber 96, the diaphragm 22 is lifted off the standpipe 98 thus opening valve 38. With valve 38 open, fluid passes into the intermediate passageway 74. Because air is compressed more readily than fluid, if air is trapped in the pumping chamber 20, sufficient pressure will not be generated in the pumping chamber 20 and outlet pressure chamber 96 to lift tire diaphragm 22 off the standpipe 98. This disables the intravenous metering device 10 which acts as a safety means to prevent air from being pumped downstream to the patient.

From the intermediate passageway 74, the fluid enters the pressure measuring chamber 70. Provided at the opening to the pressure measuring chamber 70 is a one-way flapper valve 100 carried on a molded ramp 102 formed integrally as part of cassette housing 30. The flapper valve 100 is integrally molded as part of diaphragm 22 to be biased against the molded ramp 102. The flapper valve 100 thus acts as a valve to allow fluid to pass into the pressure measuring chamber 70 but to prevent fluid from flowing back into the intermediate passageway 74 and back to the pumping chamber 20. Also extending downwardly is a biasing ridge 79 which acts to bias flapper valve 100 against molded ramp 102, as seen in FIG. 5.

The diaphragm 22 further includes an integrally molded priming stem 110 extending from the diaphragm 22 above the outlet valve 38 portion. The priming stem 110 includes an upper increased diameter portion 111 integrally formed with a stem base 113 thereby defining a stem flange 115. The priming stem 110 can be pulled to manually lift the diaphragm 22 off the standpipe 98 to open the pumping chamber outlet 26. In addition, formed in the housing lid surrounding the priming stem 110 is stem lock housing 112. The stem lock housing 112 includes a stem locking groove 114, best seen in FIG. 5, in which the stem flange 115 can rest. Also, as best seen in FIG. 2, the stem lock housing 112 is generally formed as an arrow to direct the user to the stem locking groove 114.

Prior to use, the intravenous metering device must be primed to eliminate air from the device. When intravenous metering device 10 is to be primed, the device is inverted, and the priming stem 110 is pulled such that the diaphragm 22 is lifted off the standpipe 98 to open the pumping chamber outlet 26 so as to allow the sequential passage of fluid from metering device inlet 49 through the air retention chamber 40 and the pumping chamber 20 to the distal pressure measuring chamber 70 to the outlet tubing 18. With the device inverted each of the chambers 20 and 40 are primed by directing the fluid into the bottom and allowing the fluid to fill the chambers upwardly. Such relatively constant fluid flow assures the elimination of air prior to use of the intravenous metering device 10, consequently enabling the intravenous metering device 10 to administer fluid free of air bubbles to a patient.

Following the priming operation, the intravenous metering device 10 is returned to its upright position and inserted into metering device control unit 12. Incoming fluid, transmitted by tubing 16 to the intravenous metering device inlet 49, subsequently passes into the air retention chamber 40 which, due to the downward extension of tubular conduit 58, prevents any air from entering the pumping chamber 20 and allows for the generation of a air-fluid interface in air retention chamber upper portion 50. Fluid free of air bubbles passes from the air retention chamber lower portion 54 through passageway 56. When valve actuator 34 is reciprocated upwardly, fluid free of air bubbles is allowed to pass into pumping chamber 20. Valve actuator 34 is then closed. As the flexible diaphragm 22 is moved downwardly by means of the pumping piston the volume within pumping chamber 20 is decreased and the pressure within pumping chamber 20 and outlet pressure chamber 96 lifts the diaphragm 22 off the standpipe 98, thereby allowing a precise amount of metered fluid to be pumped from pumping chamber 20 through the intravenous metering device outlet 72 to a patient.

Figure 7:
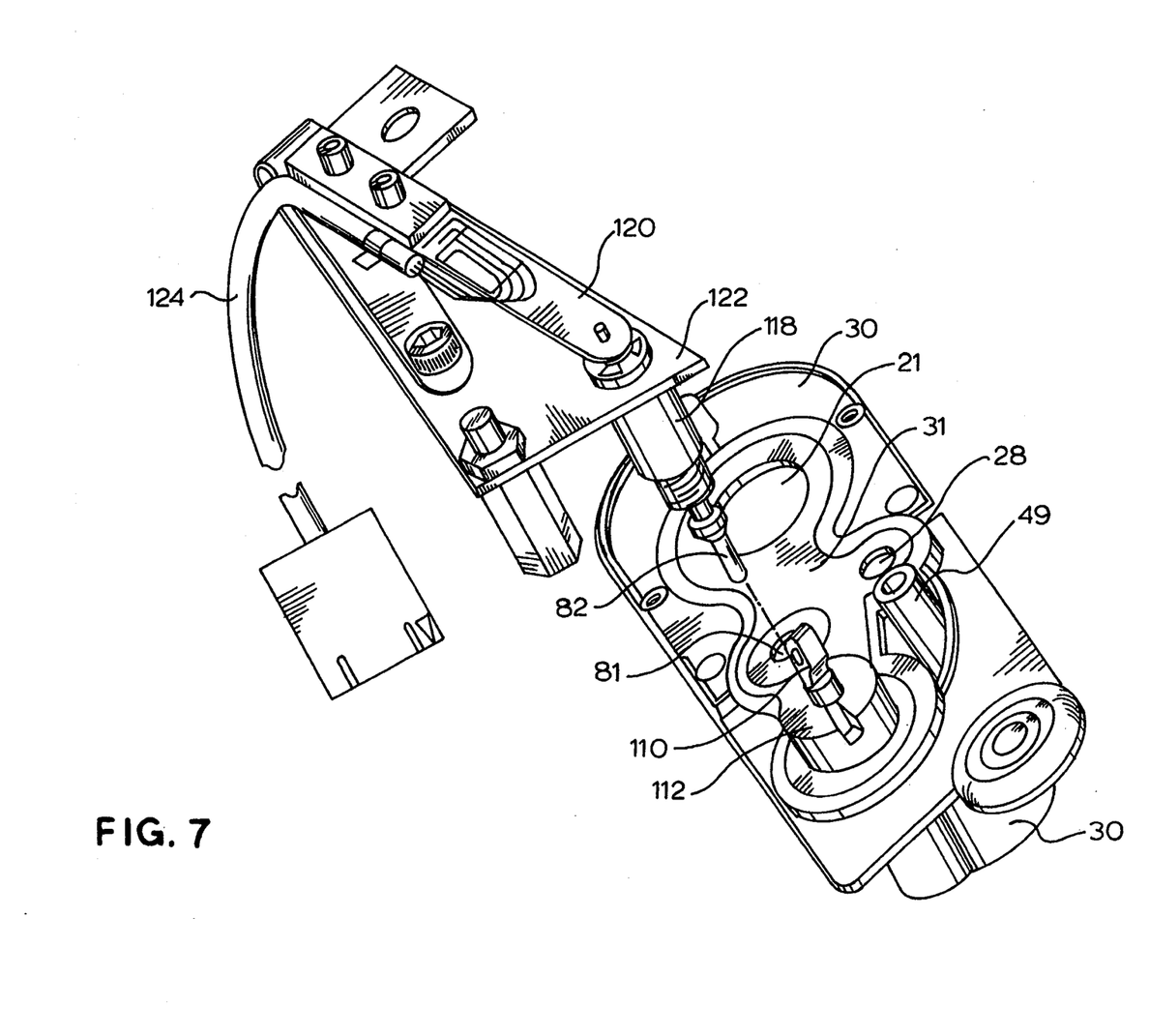
FIG. 7 is a perspective cutaway view of hardware used in accordance with the principles of the present invention.

Referring now to FIG. 7, the housing employing the pressure pin 82 is seen in a detailed view which eliminates the additional pump housing. As previously seen, the pressure pin 82 is inserted and is held by a generally funnel shaped aperture 81 in the diaphragm. In this arrangement changes in pressure in the pressure measuring chamber 70 cause the funnel shaped aperture to expand and contract. This results in movement of the pressure pin 82 in accordance with changes in pressure in the pressure measuring chamber 70.

The pressure pin 82 is contained in housing 118 and is connected to a strain gauge means. In the preferred embodiment, the strain gauge means is a balanced metal beam 120. The balanced metal beam 120 is flexed as the pressure pin 82 is moved in response to changes in the pressure in pressure measuring chamber 70. The balanced metal beam 120 acts as known in the art as a voltage divider to provide voltage signal which varies as the metal beam 120 is flexed. The pressure pin housing 118 is secured to a strain gauge bracket 122 which secures the housing 118 in the proper orientation in the pump. Additionally, an electrical connection 124 is provided between the metal beam 120 and strain gauge circuitry which will be described in detail below.

Figure 8:
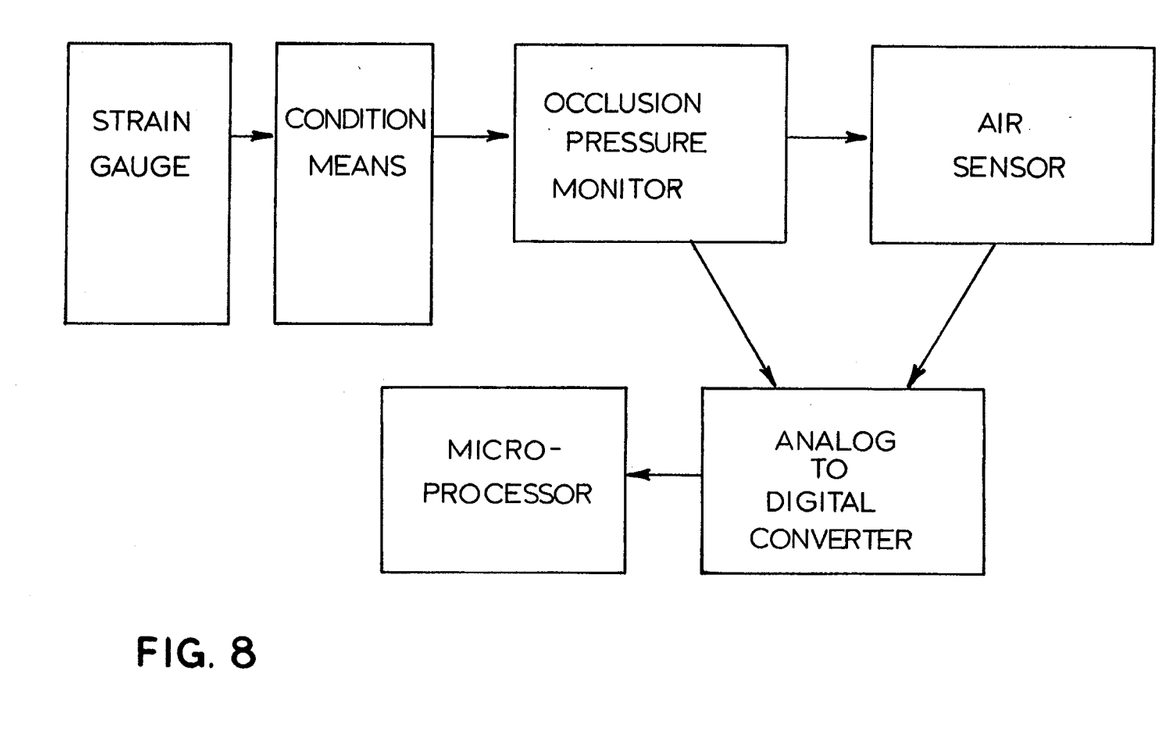
FIG. 8 is a block diagram showing the logical circuit of the present invention.

Referring now to FIG. 8, the logical circuit of the present invention is seen. The present invention includes strain gauge means which is connected through conditioning means to an occlusion pressure monitoring means. The occlusion pressure output is further connected to air sensing means. The output of both the occlusion pressure monitor and the air sensor are inputted into a analog to digital convertor. The analog to digital convertor is monitored by a microprocessor which signals when the digital signal is outside of the normal range.

Figure 9:
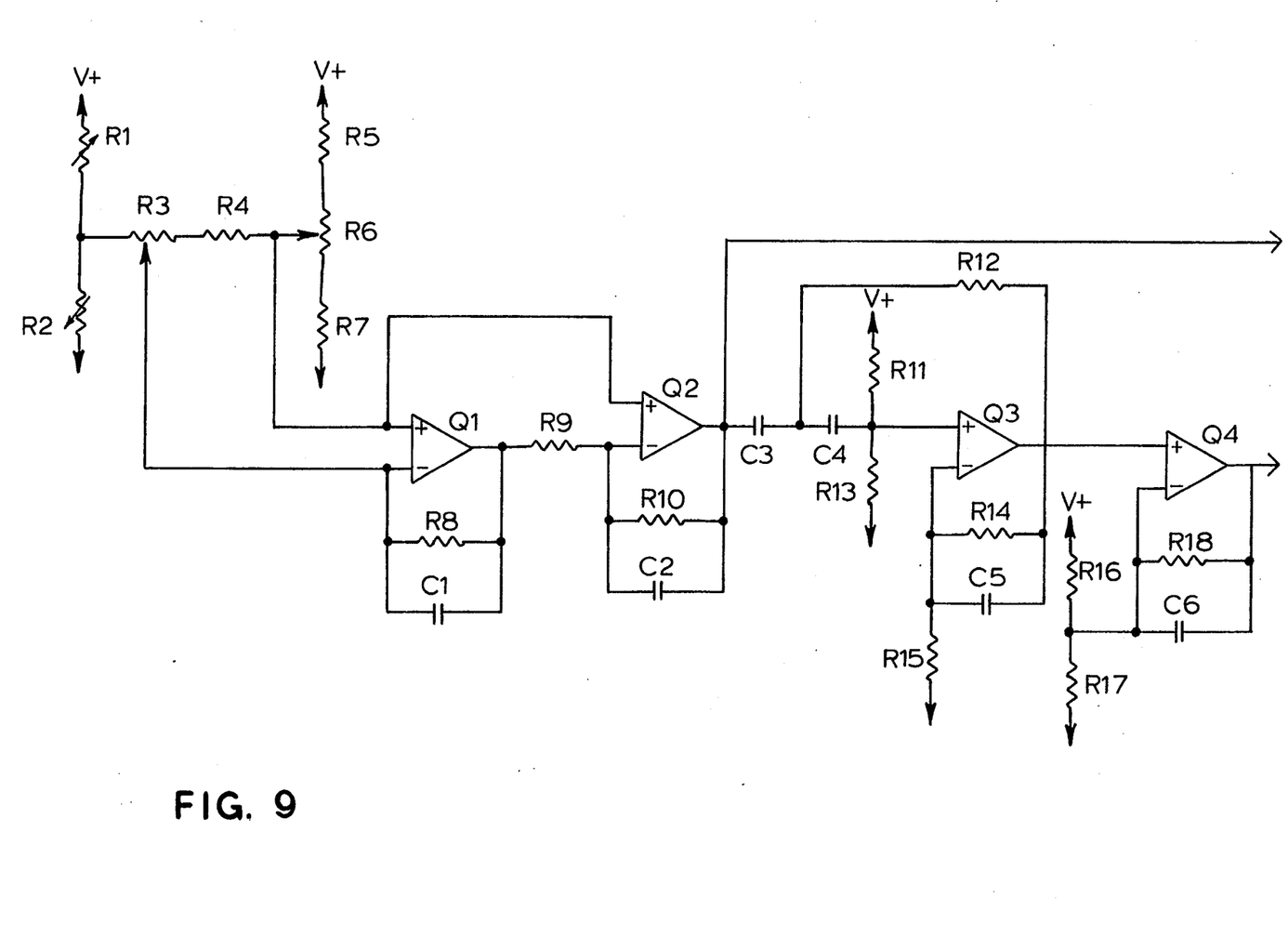
FIG. 9 is a detailed schematic of the electric circuit of the present invention.

Referring to FIG. 9, a first preferred embodiment of the flow monitoring circuit is seen. Initially, the strain gauge circuitry will be described. A pair of variable resistors R1,R2 are connected in series between the power source V+ and ground. Thus, resistors R1,R2 act as a voltage divider. The variable resistors R1,R2 comprise a balanced metal beam. As the balanced metal beam is flexed the resistance varies proportionally. This acts to vary the voltage being supplied at the junction of resistors R1,R2.

The junction of resistors R1,R2 is connected to a variable resistor R3 in series with a resistor R4. The series resistors R3,R4 are connected to a variable resistor R6. Variable resistor R6 is set by resistors R5,R7 wherein resistor R5 is connected between resistor R6 and the power source V+ while resistor R7 is connected between resistor R6 and ground. Resistor R6 acts to null the offset voltage at the junction of resistors R1,R2. Resistor R3 is provided to adjust the gain of the system to appropriate values.

An operational amplifier Q1 is provided. Operational amplifier Q1 includes a low pass feedback network which also sets gain and helps to assure stability. The low pass feedback network includes a feedback resistor R8 in parallel with a capacitor C1. The high input of operational amplifier Q1 is connected to the junction of resistors R4,R6. The low input of operational amplifier Q1 is connected to variable resisitor R3. Thus, operational amplifier Q1 provides a variable gain set by variable resistor R3 and an offset voltage set by variable resistor R6. Operational amplifier Q1 together with input circuitry acts as a means for electrically conditioning the reading of the strain gauge circuitry.

A second operational amplifier Q2 is provided. Operational amplifier Q2 includes a low pass feedback network which includes a feedback resistor R10 in parallel with a capacitor C2. The low pass feedback network further acts to assist in setting of operational amplifier Q2 and helps to assure stability.

The high input of operational amplifier Q2 is also connected to the junction of resistors R4,R6. The low input is connected to the output of operational amplifier Q1 through a resistor R9. Thus, operational amplifier Q2 along with its connecting circuitry acts as occlusion circuit means for monitoring the strain gauge signal. The output of operational amplifier Q2 contains the in-line pressure signal and is carefully calibrated such that a direct repeatable relation exists between voltage and pressure.

The output of operational amplifier Q2 is connected through series capacitors C3,C4 to the high input of a third operational amplifier Q3 forming a high pass filter. Operational amplifier Q3 includes a low pass feedback network which includes a feedback resistor R14 in parallel with a capacitor C5. The feedback network assists in setting the gain of operational amplifier Q3, helps to assure stability and also forms a band pass function with a preferred gain of two.

The output of operational amplifier Q3 is also fed back via a resistor R12 to the junction of capacitors C3,C4. The high input of operational amplifier is further connected to voltage dividing resistors R11,R13. The junction of series resistors R11,R13 is input into the high input of operational amplifier Q3, with resistor R11 connected to the power source V+ and resistor R13 connected to ground. The low input of operational amplifier Q3 is further connected to ground through a resistor R15.

The output of operational amplifier Q3 is inputted into the high input of a fourth operational amplifier Q4. Operational amplifier Q4 includes a low pass feedback network to assist in setting the gain of operational amplifier Q4 and help to assure stability which includes a feedback resistor R18 in parallel with a capacitor C6. The low input of operational amplifier Q4 is further connected to the junction of voltage divider series resistors R16,R17, with resistor R16 connected to the power source V+ and resistor R17 connected to ground. The output of operational amplifier Q4 contains the in-line or in-cassette gas signal information.

Figure 10:
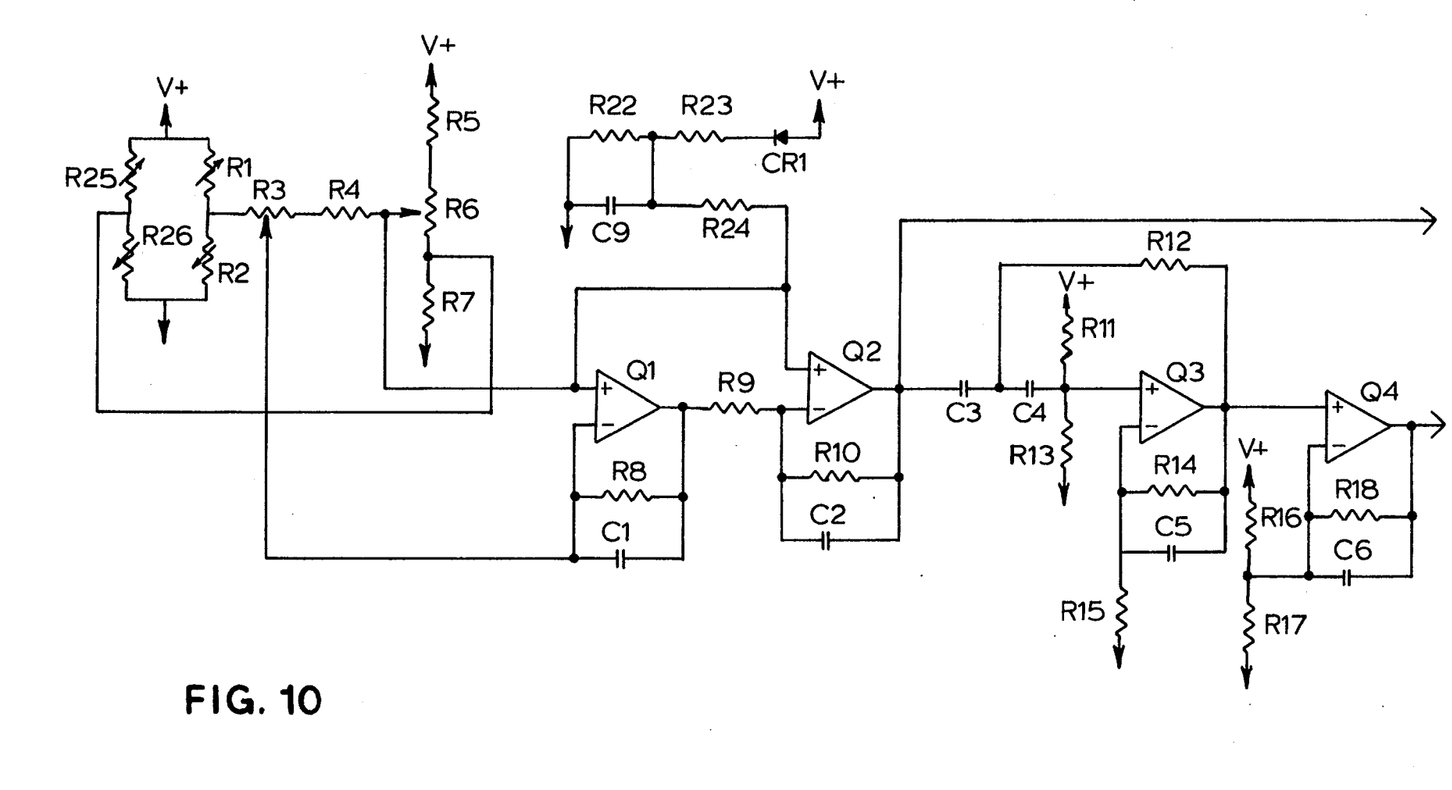
FIG. 10 is a detailed schematic of an alternative preferred electric circuit in accordance with the principles of the present invention.

Referring now to FIG. 10, an alternative preferred embodiment of the flow monitoring circuit is seen. In the circuit, like elements are designated by like designations and for brevity the discussion is limited to only those additional elements not previously discussed in reference to FIG. 9.

The alternative circuit includes an additional set of series variable resistors R25,R26 which act as a voltage divider connected between the power supply V+ and ground. The junction of resistors R25,R26 is connected to the junction of resistor R7 and variable resistor R6 of the offset adjust circuit. Thus, resistors R25,R26 act with resistors R1,R2 as a full bridge strain gauge which improves the sensitivity of the strain gauge by preferably a factor of four.

The alternative circuit further includes means for electrically offsetting the strain gauge. The electrical offset means is provided to balance a forced mechanical offset of the balanced metal beam to achieve linearity. In particular, a specific connection is provided between the junction of resistor R6 and resistor R7 of the offset adjust circuit and the junction of resistor R25 and resistor R26 of the full bridge strain gauge to create this condition. The forced mechanical offset is created by an adjustment screw (not shown) and is extended by insertion of the cassette into the pumping mechanism.

The alternative preferred embodiment further includes means for compensating temperature changes. Particularly, the high input of operational amplifier Q2 is further connected to a resistor R24 which is connected in series to a second resistor R23. Resistor R23 is connected to power source V+ through a diode CR1. The junction of resistor R24 and resistor R23 is connected to ground through a resistor R22 and a parallel capacitor C9. The voltage change due to temperature changes in the diode characteristic compensates nominal temperature changes in the rest of the circuitry.

It should be understood that various modifications, changes and variations may be made in the arrangement, operations and details of construction of the elements disclosed herein without departing from the spirit and scope of the invention.

What is claimed is:

1. An apparatus for monitoring the intravenous metering of liquid to a patient comprising:
    a flexible balanced metal beam in communication with a pressure measuring chamber such that the balanced metal beam flexes in response to changing pressure conditions in the metering of liquids, with the flex of the balanced metal beam providing an electronic signal which varies as a function of the pressure conditions;
    occlusion circuit means having as an input the electronic signal provided by the balanced metal beam for monitoring the electronic signal to provide notification when the metering of liquids is precluded; and
    air sensing circuit means having as an input an electronic signal from the occlusion circuit means for monitoring the occlusion circuit signal to provide a notification when the metering of liquids further includes gas.

2. The apparatus of claim 1 further including conditioning circuit means having as an input the electronic signal from the balanced metal beam and outputting a conditioned electronic signal to the occlusion circuit means.

3. The apparatus of claim 1 further wherein the occlusion circuit means provides a refined electronic signal as input to the air sensing circuit means.

4. The apparatus of claim 1 wherein the balanced metal beam further includes a voltage divider to provide the electronic signal.

5. The apparatus of claim 1 wherein the occlusion circuit means comprises an operational amplifier.

6. The apparatus of claim 1 wherein the air sensing circuit means comprises a pair of series amplifiers.

7. An apparatus for monitoring the conditions in an intravenous metering device having upstream and downstream tubing comprising:
    a flexible balanced metal beam in communication with a pressure measuring chamber in the intravenous metering device, the balanced metal beam flexing in response to changing pressure conditions, the flex of the balanced metal beam providing an electronic signal which varies in accordance with pressure conditions in the intravenous metering device;
    occlusion sensing circuit means having as an input the electronic signal for sensing the providing a notification when liquid is precluded from flowing into the metering device; and
    air sensing circuit means having as an input the strain gauge signal for sensing and providing a notification when a gas is present in the metering device.

8. The apparatus of claim 7 further including condition circuit means having as an input the electronic signal from the balanced metal beam and outputting a conditioned electronic signal to the occlusion sensing circuit means and the air sensing circuit means.

9. The apparatus of claim 7 further wherein prior to inputting into the air sensing circuit means the electronic signal has been inputted into the occlusion sensing circuit means which output is inputted into the air sensing circuit means.

10. A system for metering liquids for delivery from a source of liquid to a patient comprising:
    an intravenous metering device having a pressure measuring chamber in fluid communication with the liquid;
    a pressure pin functionally associated with the pressure measuring chamber such that changes in the pressure measuring chamber result in movement of the pressure pin;
    a flexible balanced metal beam in contact with the pressure pin such that the balanced metal beam flexes in response to movement of the pressure pin, the flexible balanced metal beam further providing an electronic signal which varies as a function of the flex of the balanced metal beam; and
    electronic circuit means for monitoring the balanced metal beam electronic signal and providing notification when liquid flow through the intravenous metering device is precluded and for monitoring the balanced metal beam electronic signal and providing notification when gas is present in the intravenous metering device.

* * * * *